United States Patent
Mace et al.

(10) Patent No.: US 8,586,077 B2
(45) Date of Patent: Nov. 19, 2013

(54) NUTRITIONAL COMPOSITION FOR INFANTS

(75) Inventors: Catherine Mace, Lausanne (CH); Olivier Kevork Aprikian, Dublin, OH (US); Etienne Pouteau, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/145,042

(22) PCT Filed: Dec. 16, 2009

(86) PCT No.: PCT/EP2009/067297
§ 371 (c)(1),
(2), (4) Date: Jul. 18, 2011

(87) PCT Pub. No.: WO2010/081604
PCT Pub. Date: Jul. 22, 2010

(65) Prior Publication Data
US 2012/0004163 A1 Jan. 5, 2012

(30) Foreign Application Priority Data

Jan. 19, 2009 (EP) .................................. 09150858

(51) Int. Cl.
*A61K 38/00* (2006.01)
*A23K 1/17* (2006.01)
(52) U.S. Cl.
USPC .............................. 424/442; 514/4.8; 514/5.5
(58) Field of Classification Search
USPC .................... 424/442; 514/4, 8, 5.5
See application file for complete search history.

(56) References Cited

U.S. PATENT DOCUMENTS

| | | |
|---|---|---|
| 6,787,158 B1 | 9/2004 | Erdmann et al. |
| 2008/0108548 A1* | 5/2008 | Luyer et al. ................... 514/2 |
| 2010/0092610 A1* | 4/2010 | Haschke et al. ............... 426/61 |

FOREIGN PATENT DOCUMENTS

| | | |
|---|---|---|
| EP | 880902 | 12/1998 |
| WO | 0178530 | 10/2001 |
| WO | WO 01/78530 | * 10/2001 |
| WO | 2007004878 | 1/2007 |
| WO | 2008054192 | 5/2008 |

OTHER PUBLICATIONS

Korotkova Marina et al: "Leptin levels in rat offspring are modified by the ratio of linoleic to alpha-linolenic acid in the maternal diet"; Journal of Lipid Research, vol. 43, No. 10, Oct. 2002, pp. 1743-1749, XP002528923.

Massiera Florence et al: "Arachidonic acid and prostacyclin signaling promote adipose tissue development: A human health concern?" Journal of Lipid Research, vol. 44, No. 2, Feb. 2003, pp. 271-279, XP002528921.

Ailhaud G et al: "Fatty acid composition of fats is an early determinant of childhood obesity: a short review and an opinion." Obesity Reviews: An Official Journal of the International Association for the Study of Obesity Feb. 2004, vol. 5, No. 1, Feb. 2004, pp. 21-26, XP002528922.

(Continued)

*Primary Examiner* — Aradhana Sasan
(74) *Attorney, Agent, or Firm* — K&L Gates LLP

(57) ABSTRACT

A nutritional composition for infants comprises a protein source, a lipid source and a carbohydrate source wherein the lipid source includes at least 16 wt % linoleic acid and at least 2 wt % α-linolenic acid expressed as a percentage of total fatty acid content in each case and in amounts such that the ratio of linoleic acid:α-linolenic acid is in the range from 1 to 10.

6 Claims, 4 Drawing Sheets

(56) References Cited

OTHER PUBLICATIONS

Korotkova M et al: "Maternal Dietary Intake of Essential Fatty Acids Affects Adipose Tissue Growth and Leptin MRNA Expression in Suckling Rat Pups" Pediatric Research, Williams and Wilkins, Baltimore, MD, US, vol. 52, No. 1, Jul. 1, 2002, pp. 78-84, XP001120109.

Neese, et al., "Advances in the Stable Isotope-Mass Spectrometric Measurement of DNA Synthesis and Cell Proliferation," Analytical Biochemistry, 2001, vol. 298, 7 pages.

Hellerstein, et al., "Mass isotopomer distribution analysis at eight years: theoretical, analysis and experimental considerations," Am. J. Physiol., 1999, vol. 276, pp. E1146-E1170.

PCT International Search Report for International Application No. PCT/EP2009/067297 mailed on Feb. 25, 2010.

* cited by examiner

NUTRITIONAL COMPOSITION FOR INFANTS

This invention relates to a nutritional composition, more specifically to a nutritional composition for infants which may help to reduce the risk of development of obesity later in life.

Mother's milk is recommended for all infants. However, in some cases breast feeding is inadequate or unsuccessful or inadvisable for medical reasons or the mother chooses not to breast feed either at all or for a period of more than a few weeks. Infant formulas have been developed for these situations.

The prevalence of obesity and overweight in adults, children and adolescents has increased rapidly over the past 30 years in the United States and globally and continues to rise. Childhood overweight and obesity currently affects 18 million children under age 5 worldwide. Almost 30% of US children and adolescents and between 10 and 30% of European children are overweight or obese.

Increasingly it is believed that the first 6 months of life represent one of the most important postnatal periods for human fat mass development and consequently may be a critical window for programming excess of adiposity later in life. Moreover, human epidemiological data and animal studies evidence that elevated body weight at birth or during infancy are associated with a risk for development of diseases such as metabolic syndrome, Type 2 diabetes and cardiovascular problems later in life.

Korotkova et al. investigated the influence of the ratio of linoleic acid (LA) to α-linolenic acid (ALA) in the maternal diet on serum leptin levels in their suckling pups and found that feeding dams a diet rich in ALA (LA/ALA ratio 0.42) decreased serum leptin levels in the suckling pups compared with pups whose mothers were fed a diet containing both LA and ALA (LA/ALA ratio 9.0). Mean serum leptin levels of a third group of pups whose mothers had been fed a diet rich in LA (LA/ALA ratio 216) were between the levels in the other two groups but not significantly different from either. The authors chose to study serum leptin levels in the pups as a number of earlier studies already suggest that circulating leptin levels during the perinatal period could be important for normal development and health. On the basis of their findings, they go on to predict that it could be the balance between LA and ALA in the maternal diet rather than the amount of LA or ALA per se that is important for adipose tissue growth (Korotkova et al, "Leptin levels in rat offspring are modified by the ratio of linoleic to α-linolenic acid in the maternal diet", Journal of Lipid Research, Vol 43, 2002, pages 1743-1749).

In WO2008/054192, it is claimed that the whole adipose tissue mass of infants is not a good predictor to determine the risks of diseases later in life and that it is rather the accumulation of visceral fat mass in early infancy that should be considered. It has been demonstrated that visceral adipocyte count is primarily determined during infancy and the inventors of WO2008/054192 believe that it would be useful to be able to control visceral adipogenesis during this period. The solution proposed in WO2008/054192 is to reduce the amount of LA fed to infants such that the LA/ALA ratio is between 2 and 6 whilst at the same time ensuring that LA amounts to less than 14.5% by weight of total fatty acids.

However, this approach may have practical limitations as regards nutrition of human infants given that both LA and ALA are essential fatty acids, that is, fatty acids which cannot be synthesized by the body.

There is, therefore, clearly a need for alternative nutritional approaches aimed at reducing accumulation of fat mass during childhood and thus reducing risk of developing obesity later in life as well as the risk of developing diseases associated with such obesity.

SUMMARY OF THE INVENTION

The present inventors have surprisingly found that feeding a composition relatively rich in α-linolenic acid during infancy reduces accumulation of total fat mass later in life.

Accordingly, the present invention provides a nutritional composition comprising a protein source, a lipid source and a carbohydrate source wherein the lipid source includes at least 16 wt % linoleic acid and at least 2 wt % α-linolenic acid expressed as a percentage of total fatty acid content in each case and in amounts such that the ratio of linoleic acid:α-linolenic acid is in the range from 1 to 10.

The invention also extends to the use of linoleic acid and α-linolenic acid in the manufacture of a nutritional composition for administration to an infant in the first six months of life of the infant so as to reduce the risk of development of obesity later in life wherein the composition includes at least 16 wt % linoleic acid and at least 2 wt % α-linolenic acid expressed as a percentage of total fatty acid content of the composition in each case and in amounts such that the ratio of linoleic acid:α-linolenic acid is in the range from 1 to 10.

The invention further extends to a method of reducing the risk that an infant will develop obesity later in life comprising feeding to the infant in the six months of its life a nutritional composition comprising a protein source, a lipid source and a carbohydrate source wherein the lipid source includes at least 16 wt % linoleic acid and at least 2 wt % α-linolenic acid expressed as a percentage of total fatty acid content in each case and in amounts such that the ratio of linoleic acid:α-linolenic acid is in the range from 1 to 10.

Without wishing to be bound by theory, the present inventors believe on the basis of their experimental observations that feeding a diet rich in α-linolenic acid during infancy may in some way reduce either or both of adipogenesis and increase in size of adipocytes and that these beneficial effects may persist in later life, thus reducing the risk of development of obesity later in life. Further, obesity is known to be associated with increased risk of conditions such as insulin resistance and glucose intolerance which may lead to development of Type 2 diabetes.

DETAILED DESCRIPTION OF THE INVENTION

Figure 1:
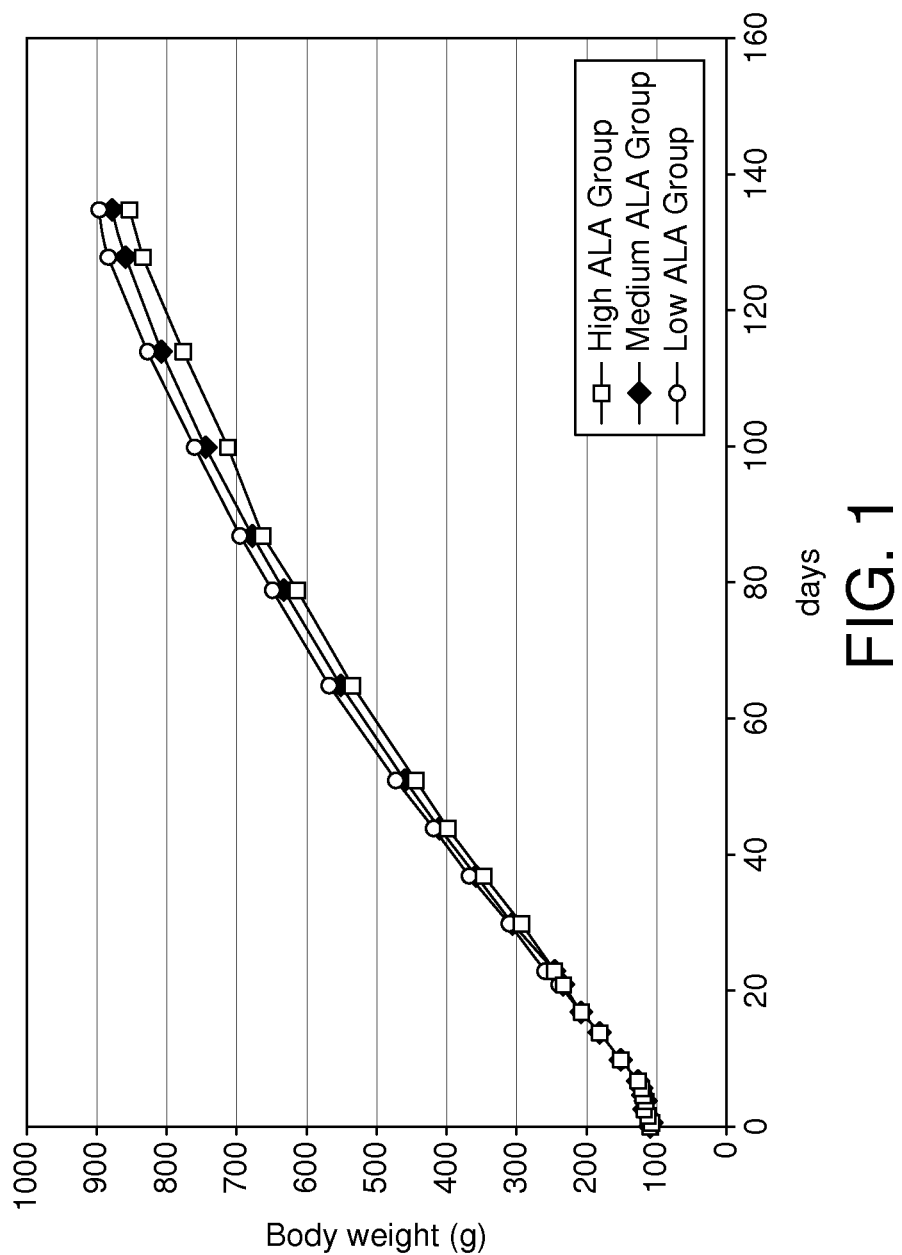
FIG. 1 shows the evolution of body weight of three groups of guinea pig pups fed different diets over the first 136 days of life.

In this specification, the following expressions have the meanings assigned to them below:—

"ALA" means α-linolenic acid (C18:3n-3);
"infant" means a child under the age of 12 months and "infancy" shall be construed accordingly; For the purpose of the present document the term "infant" comprises young baby animals, such as young pets, young dogs, young horses or young cats.
"LA" means linoleic acid (C18:2n-6);
"later in life" means, in the context of an infant, any point in life after completion of infancy. One example of such a point would be at the age of the adiposity rebound which, in human infants, typically occurs between the ages of five and six years.

All percentages and ratios are by weight unless otherwise specified.

A nutritional composition according to the present invention comprises at least 16% LA and at least 2% ALA. Preferably the LA content is in the range from 18 to 30% of total fatty acids, more preferably 18 to 25%. Preferably the ALA content is in the range from 2 to 12% of total fatty acids, more preferably from 6 to 11%. The LA:ALA ratio is preferably in the range from 2 to 6.

Preferably, the nutritional composition of the present invention has a protein content of less than 1.85 g/100 kcal. The detailed make-up of the protein source is not believed to be critical to the present invention provided that the minimum requirements for essential amino acid content are met and satisfactory growth is ensured. Thus, protein sources based on cows' milk proteins such as whey, casein and mixtures thereof may be used as well as protein sources based on soy. However, mixtures of whey and casein proteins are preferred. The casein:whey ratio may lie in the range from 70:30 to 30:70 but is preferably 30:70.

The protein(s) in the protein source may be intact or partially hydrolysed or a mixture of intact and hydrolysed proteins may be used. The protein source may additionally be supplemented with free amino acids if this is necessary to meet the minimum requirements for essential amino acid content. These requirements are published for example in EC Directive 2006/141/EC.

As noted above, the preferred protein source is a mixture of casein and whey proteins. The whey protein may be a whey protein isolate, acid whey, sweet whey or sweet whey from which the caseino-glycomacropeptide has been removed (modified sweet whey).

Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. A process for removing CGMP from sweet whey is described in EP 880902.

If modified sweet whey is used as the whey protein in a mixture of 70% whey and 30% casein, the protein source may be supplemented by free histidine in an amount between 0.1 and 0.3% of total protein content.

The nutritional composition of the present invention contains a source of carbohydrates. The preferred source of carbohydrates is lactose although other carbohydrates such as saccharose, maltodextrin, and starch may also be added. Preferably, the carbohydrate content of the nutritional composition is between 9 and 14 g/100 kcal.

The nutritional composition of the present invention contains a source of lipids. In addition to LA and ALA, the lipid source may include any lipid or fat which is suitable for use in nutritional compositions to be fed to infants. Preferred fat sources include coconut oil, low erucic rapeseed oil (canola oil), soy lecithin, palm olein, and sunflower oil. The lipid source may also include small amounts of preformed long chain polyunsaturated fatty acids arachidonic acid (C20:4n-6) and docosahexaenoic acid (C22:6n-3). Fish oils are a suitable source of docosahexaenoic acid, alternatively single cell microbial oils are suitable sources of both arachidonic acid and docosahexaenoic acid. In total, the lipid content may be between 4.4 and 6 g/100 kcal. The ratio of arachidonic acid:docosahexaenoic acid in the lipid source is preferably between 2:1 and 1:1.

The nutritional composition may also contain all vitamins and minerals understood to be essential in the daily diet in nutritionally significant amounts. Minimum requirements have been established for certain vitamins and minerals. Examples of minerals, vitamins and other nutrients optionally present in the nutritional composition include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form.

If necessary, the nutritional composition may contain emulsifiers and stabilisers such as soy lecithin, citric acid esters of mono- and di-glycerides, and the like. This is especially the case if the composition is provided in liquid form.

The nutritional composition may optionally contain other substances which may have a beneficial effect such as probiotic bacteria, fibres, lactoferrin, nucleotides, nucleosides, and the like in the amounts customarily found in nutritional compositions to be fed to infants.

The nutritional composition may be prepared in any suitable manner. For example, a nutritional composition may be prepared by blending together the protein source, the carbohydrate source, and the lipid source in appropriate proportions. If used, emulsifiers may be included in the blend at this stage. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled and any heat sensitive components; such as vitamins and minerals may be added. The pH and solids content of the homogenised mixture is conveniently standardised at this point.

If it is desired to produce a powdered composition, the homogenised mixture is transferred to a suitable drying apparatus such as a spray drier or freeze drier and converted to powder. The powder should have a moisture content of less than about 5% by weight.

If it is desired to produce a liquid composition, the homogenised mixture is filled into suitable containers; preferably aseptically. However, the liquid composition may also be retorted in the container. Suitable apparatus for carrying out filling of this nature is commercially available. The liquid composition may be in the form of a ready to feed composition having a solids content of about 10 to about 14% by weight or may be in the form of a concentrate; usually of solids content of about 20 to about 26% by weight.

The invention will now be further illustrated by reference to the following examples.

Example 1

An example of the composition of a nutritional composition according to the invention is given below:—

| Nutrient | per 100 kcal | per litre |
|---|---|---|
| Energy (kcal) | 100 | 630 |
| Protein (g) | 1.5 | 9.45 |
| (skimmed milk powder, modified sweet whey) | | |
| free histidine (mg) | 2.5 | 15.8 |
| casein:whey ratio | 40:60 | 40:60 |
| Fat (g) | 5.3 | 33.4 |
| Linoleic acid (g) | 1.0 | 6.6 |
| α-Linolenic acid (g) | 0.5 | 3.3 |
| DHA (mg) | 11.5 | 72.5 |
| ARA (mg) | 11.5 | 72.5 |
| Linoleic acid: α-Linolenic acid | 2 | 2 |
| Lactose (g) | 11.6 | 73.1 |
| Minerals and Electrolytes | | |
| Na (mg) | 25 | 158 |
| K (mg) | 89 | 561 |
| Cl (mg) | 64 | 403 |
| Ca (mg) | 64 | 403 |
| P (mg) | 32 | 202 |
| Ca/P | 2.0 | 2.0 |
| Mg (mg) | 6.9 | 43.5 |
| Mn (µg) | 8.0 | 50.4 |
| Vitamins and Trace Elements | | |
| Vitamin A (IU) | 350 | 2205 |
| Vitamin D (IU) | 60 | 378 |
| Vitamin E (IU) | 1.2 | 7.6 |
| Vitamin K1 (µg) | 8.0 | 50.4 |
| Vitamin C (mg) | 10 | 63 |
| Vitamin B1 (mg) | 0.07 | 0.44 |
| Vitamin B2 (mg) | 0.15 | 0.95 |
| Niacin (mg) | 1.0 | 6.3 |
| Vitamin B6 (mg) | 0.075 | 0.47 |
| Folic acid (µg) | 12 | 75.6 |
| Pantothenic acid (mg) | 0.45 | 2.83 |
| Vitamin B12 (µg) | 0.3 | 1.89 |
| Biotin (µg) | 2.2 | 13.9 |
| Choline (mg) | 10 | 63 |
| Inositol (mg) | 5.0 | 31.5 |
| Taurine (mg) | 7.0 | 44.1 |
| Carnitine (mg) | 1.6 | 10.1 |
| Fe (mg) | 1.2 | 7.56 |
| I (µg) | 15 | 94.5 |
| Cu (mg) | 0.07 | 0.44 |
| Se (µg) | 2.0 | 12.6 |
| Zn (mg) | 0.75 | 4.72 |

| Nutrient | per 100 kcal | per litre |
|---|---|---|
| Nucleotides | | |
| CMP (mg) | 2.3 | 14.5 |
| UMP (mg) | 1.5 | 9.5 |
| AMP (mg) | 0.7 | 4.4 |
| GMP (mg) | 0.3 | 1.9 |

A nutritional composition according to the invention may be fed to an infant as the sole source of nutrition from birth to the age of four to six months and subsequently as part of a mixed diet during the introduction of solid foods until weaning is complete at about the age of 12 months.

Example 2

This example investigates the effect of feeding diets containing different amounts of LA and ALA to newborn guinea pig pups on the development of total fat mass of the pups in the post-weaning period. The infant guinea pig is considered to be a good animal model to study to predict the development fat mass in human infants because, like newborn human infants, newborn guinea pig pups are born with an appreciable amount of body fat whilst newborn rat pups are very lean.

Study Design:

Newborn male guinea pigs were divided into three groups with 20 animals in each group. Each group was fed a suckling/weaning diet in which 44% of the energy was supplied by fat for 21 days. The different diets were isocaloric and differed only in their ALA contents. The high ALA diet contained 10% ALA based on total fatty acids, the medium ALA diet contained 2.4% ALA based on total fatty acids and the low diet contained 0.85% ALA based on total fatty acids. The levels of LA were kept relatively constant between diets such that the LA:ALA ratios were about 2, 10 and 30 respectively. Further details of the fatty acid composition of the three diets are given in Table 1.

TABLE 1

| Fatty acid composition of the suckling/weaning diets: | | | |
|---|---|---|---|
| % of total fatty acids | 10% ALA | 2.4% ALA | 0.8% ALA |
| C12:0 | 7.1 | 8.2 | 7.9 |
| C14:0 | 3.4 | 3.9 | 3.7 |
| C16:0 | 22.7 | 22.0 | 21.8 |
| C16:1 | 0.2 | 0.1 | 0.1 |
| C18:0 | 3.0 | 3.2 | 3.0 |
| C18:1 | 33.5 | 33.0 | 33.3 |
| C18:2n-6 (LA) | 20.2 | 26.2 | 28.5 |
| C18:3n-3 (ALA) | 9.9 | 2.4 | 0.8 |
| C20:0 | 0.0 | 0.0 | 0.0 |
| C20:1 | 0.0 | 0.0 | 0.0 |
| C20:4n-6 | 0.0 | 0.0 | 0.0 |
| C20:5n-3 | 0.0 | 0.0 | 0.0 |
| C22:0 | 0.0 | 0.0 | 0.0 |
| C22:5n-3 | 0.0 | 0.0 | 0.0 |
| C22:6n-3 | 0.0 | 0.0 | 0.0 |
| LA/ALA | 2.0 | 10.7 | 33.6 |

At the end of the suckling/weaning period (day 21), all groups were fed a diet with a moderately high fat content (35% of energy from fat) containing 2% ALA and 26% LA until day 136. Body weight and fat mass were recorded at days 21, 51, 79, 107, 128 and 136 and retroperitoneal adipose tissue cellularity, plasma fatty acid composition, and insulin were recorded at day 21 and day 136.

Results:

As expected, at the end of the suckling/weaning period (day 21) the concentrations of ALA, in plasma phospholipid (Table 2) and triglyceride (Table 3) fractions, were higher in the 10% ALA group than in the other groups.

TABLE 2

Fatty acid (μg/ml) composition in plasma phospholipids at d 21.

|  | High ALA | Medium ALA | Low ALA |
|---|---|---|---|
| C10:0 | 0.1 ± 0.02 | 0.1 ± 0.03 | 0.1 ± 0.07 |
| C12:0 | 0.2 ± 0.03 | 0.2 ± 0.02 | 0.3 ± 0.13 |
| C14:0 | 0.8 ± 0.23 | 1.0 ± 0.10 | 1.1 ± 0.17 |
| C16:0 | 35.9 ± 9.1 | 49.3 ± 8.9 | 40.2 ± 3.6 |
| C17:0 | 1.2 ± 0.38 | 1.9 ± 0.41 | 1.2 ± 0.10 |
| C18:0 | 70.1 ± 23.6 | 98.6 ± 28.1 | 68.6 ± 4.2 |
| C18:1n-9 cis + trans | 23.4 ± 7.6 | 30.8 ± 7.3 | 23.2 ± 1.9 |
| C18:1n-7 cis + trans | 3.1 ± 0.8 | 6.2 ± 1.4 | 5.2 ± 0.9 |
| C18:2n-6 (LA) | 67.5 ± 22.2 | 99.0 ± 26.3 | 77.0 ± 7.5 |
| C18:3n-6 (GLA) | 0.1 ± 0.06 | 0.1 ± 0.09 | 0.2 ± 0.13 |
| C18:3n-3 (ALA) | 2.9 ± 1.8 | 0.9 ± 0.2 | 0.6 ± 0.2 |
| C20:0 | 1.2 ± 0.5 | 1.5 ± 0.2 | 0.9 ± 0.03 |
| C20:1n-9 | 0.5 ± 0.2 | 0.7 ± 0.08 | 0.6 ± 0.1 |
| C20:2n-6 | 0.8 ± 0.1 | 1.2 ± 0.1 | 1.3 ± 0.2 |
| C20:3n-6 | 0.9 ± 0.2 | 1.1 ± 0.25 | 1.0 ± 0.07 |
| C20:4n-6 (AA) | 11.4 ± 3.6 | 14.8 ± 3.0 | 11.7 ± 1.1 |
| C20:3n-3 | 0.3 ± 0.08 | 0.2 ± 0.06 | 0.1 ± 0.03 |
| C22:0 | 1.9 ± 0.9 | 2.1 ± 0.4 | 1.1 ± 0.2 |
| C22:1n-9 | 0.4 ± 0.2 | 0.4 ± 0.1 | 1.5 ± 1.0 |
| C20:5n-3 (EPA) | 0.2 ± 0.1 | 0.1 ± 0.03 | 0.1 ± 0.03 |
| C22:2n-6 | 1.1 ± 0.5 | 1.5 ± 0.2 | 0.8 ± 0.1 |
| C22:4n-6 | 1.2 ± 0.5 | 1.8 ± 0.3 | 1.2 ± 0.2 |
| C24:0 | 2.6 ± 1.2 | 3.4 ± 0.6 | 1.9 ± 0.4 |
| C24:1n-9 | 2.4 ± 0.8 | 2.8 ± 0.3 | 2.0 ± 0.5 |
| C22:5n-3 (DPA) | 2.1 ± 0.8 | 1.7 ± 0.3 | 0.9 ± 0.1 |
| C22:6n-3 (DHA) | 1.1 ± 0.4 | 1.3 ± 0.3 | 0.7 ± 0.1 |

Mean ± SEM

TABLE 3

FA (μg/ml) composition in plasma triglycerides at d 21.

|  | High ALA | Medium ALA | Low ALA |
|---|---|---|---|
| C10:0 | 0.2 ± 0.1 | 0.1 ± 0.04 | 0.2 ± 0.01 |
| C12:0 | 0.9 ± 0.2 | 1.0 ± 0.1 | 0.8 ± 0.3 |
| C14:0 | 4.0 ± 1.1 | 4.6 ± 0.7 | 4.0 ± 2.4 |
| C16:0 | 49.1 ± 10.7 | 52.8 ± 5.7 | 42.2 ± 18 |
| C17:0 | 0.9 ± 0.2 | 1.1 ± 0.2 | 0.7 ± 0.09 |
| C18:0 | 15.7 ± 3.3 | 14.4 ± 2.3 | 10.5 ± 3.5 |
| C18:1 n-9 cis | 85.0 ± 17.8 | 85.4 ± 6.0 | 63.2 ± 18 |
| C18:1 n-7 cis | 2.6 ± 0.5 | 2.8 ± 0.3 | 2.0 ± 0.6 |
| C18:2 n-6 (LA) | 72.8 ± 13.7 | 85.4 ± 6.0 | 71.1 ± 27.9 |
| C18:3n-6 (GLA) | 0.2 ± 0.2 | 0.6 ± 0.05 | 0.5 ± 0.1 |
| C18:3n-3 (ALA) | 11.1 ± 2.5 [a] | 5.1 ± 0.7 [b] | 2.7 ± 0.2 [b] |
| C20:0 | 0.5 ± 0.2 | 0.7 ± 0.1 | 0.2 ± 0.1 |
| C20:1n-9 | 1.2 ± 0.1 | 1.3 ± 0.1 | 1.1 ± 0.5 |
| C20:2n-6 | 1.4 ± 0.2 | 1.5 ± 0.2 | 1.6 ± 0.8 |
| C20:3n-6 | 0.8 ± 0.1 | 0.7 ± 0.09 | 0.6 ± 0.09 |
| C20:4n-6 (AA) | 3.7 ± 0.4 | 3.5 ± 0.3 | 3.7 ± 0.3 |
| C20:3n-3 | 0.4 ± 0.1 | 0.2 ± 0.05 | 0.1 ± 0.09 |
| C22:0 | 0.4 ± 0.04 | 0.4 ± 0.05 | 0.3 ± 0.02 |
| C22:1n-9 | 0.3 ± 0.08 | 0.2 ± 0.02 | 0.2 ± 0.03 |
| C20:5n-3 (EPA) | 0.3 ± 0.04 | 0.1 ± 0.04 | 0.1 ± 0.08 |
| C22:2n-6 | 0.3 ± 0.04 | 0.3 ± 0.06 | 0.2 ± 0.08 |
| C22:4n-6 | 0.9 ± 0.1 | 0.9 ± 0.1 | 0.9 ± 0.2 |
| C24:0 | 0.7 ± 0.1 | 0.8 ± 0.1 | 0.6 ± 0.1 |
| C22:5n-3 (DPA) | 0.8 ± 0.1 | 0.6 ± 0.1 | 0.4 ± 0.01 |
| C22:6n-3 (DHA) | 0.3 ± 0.1 | 0.3 ± 0.06 | 0.2 ± 0.05 |

Figure 2:
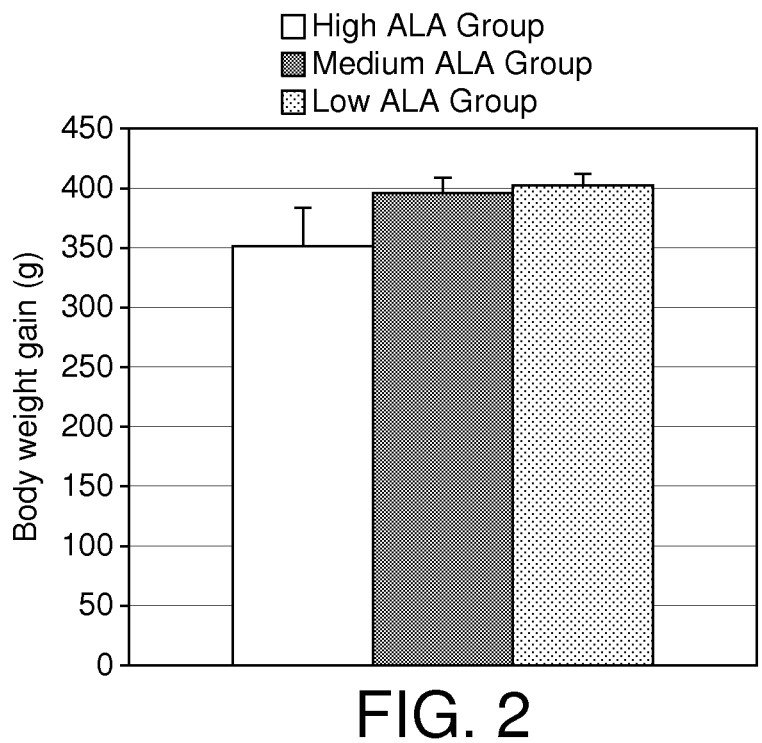
FIG. 2 shows the median body weight gain of pups in the three groups between day 21 and day 79.

Mean ± SEM
Different letters indicate statistical significance at P < 0.05, ND; not detectable As may be seen from FIG. 1, mean body weight did not differ significantly between the three groups during the course of the experiment. However, FIG. 2 shows that between day 21 and day 78 the high ALA group tended to gain less body weight than the other groups.

At the end of the suckling/weaning period (day 21), total fat mass measured by NMR did not differ between the groups. Nevertheless, on average, the diameter of adipocyte cells from retroperitoneal adipose tissue of the high ALA group tended to be smaller than in the other groups (Table 4).

TABLE 4

Adipocyte diameter.

| Groups | Cell diameter (μm) |
|---|---|
| High ALA | 27.5 ± 0.8 |
| Medium ALA | 31.1 ± 1.5 |
| Low ALA | 31.9 ± 1.7 |

Mean ± SEM

The High ALA group had a smaller number of adipocytes in the larger diameter range (from 30 to 50 μm) (Table 5).

TABLE 5

Total cell number ($\times 10^6$) per diameter range and per g of retroperitoneal adipose tissue at d 21.

| Cell diameter | 10% ALA | 2.4% ALA | 0.8% ALA |
|---|---|---|---|
| 15-19 | 1.27 ± 0.2 | 1.19 ± 0.2 | 0.91 ± 0.2 |
| 19-29 | 3.82 ± 0.6 | 3.70 ± 0.5 | 3.68 ± 0.8 |
| 30-39 | 2.18 ± 0.4 | 3.54 ± 0.2 | 4.43 ± 0.8 |
| 40-49 | 0.37 ± 0.1 | 1.47 ± 0.2 | 1.85 ± 0.7 |
| 50-60 | 0.07 ± 0.02 | 0.34 ± 0.04 | 0.49 ± 0.3 |

Mean ± SEM.

Figure 3:
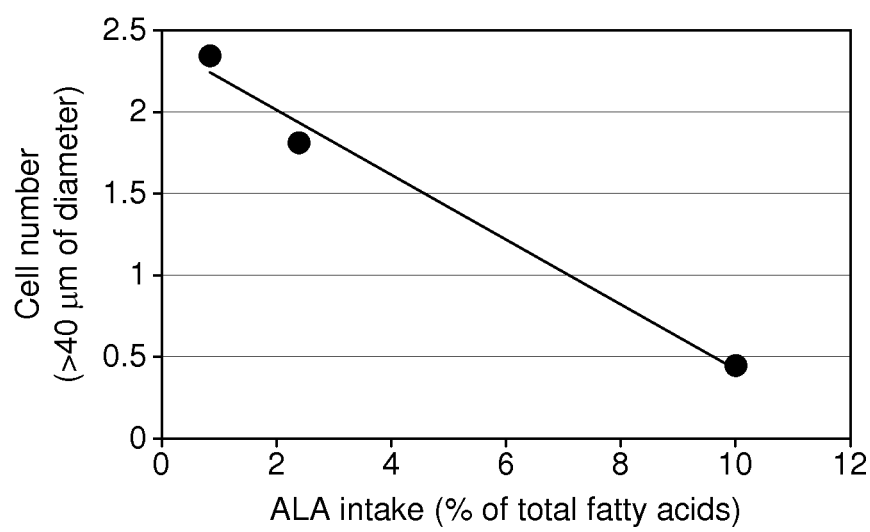
FIG. 3 shows the number of large adipocytes plotted as a function of ALA intake.

Interestingly, a dose response relationship was observed between the number of large adipocytes (>40 μm) and the percentage of ALA in the diet. As may be seen from FIG. 3, the higher was the ALA intake, the lower was the number of large adipocytes.

Figure 4:
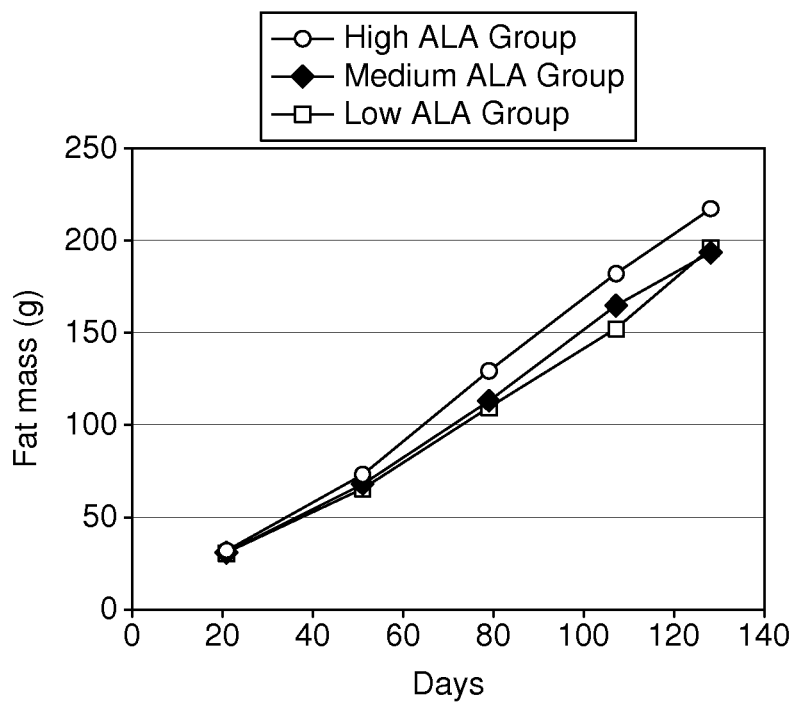
FIG. 4 shows the evolution of fat mass in the three groups expressed in grams from day 21 to day 128.
Figure 5:
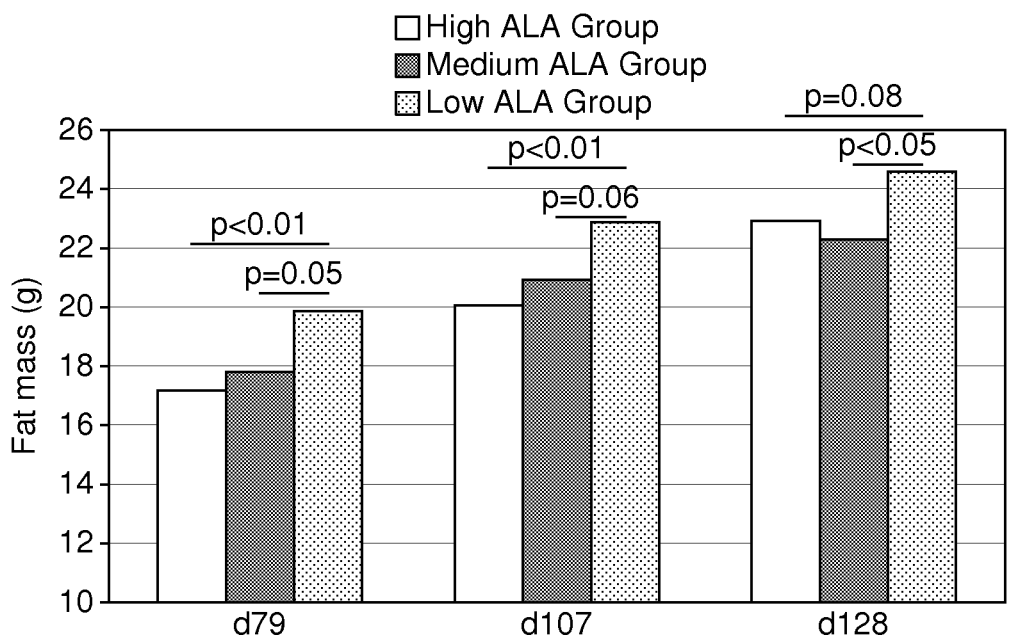
FIG. 5 shows the evolution of fat mass in the three groups expressed as a percentage of total body weight at day 79, day 107 and day 128.

Surprisingly and as may be seen from FIGS. 4 and 5, the Low ALA group had higher fat mass values in both gram and percentage values than the High ALA group at day 79 ($p<0.01$), day 107 ($p<0.01$) and day 128 ($p=0.08$).

Figure 6:
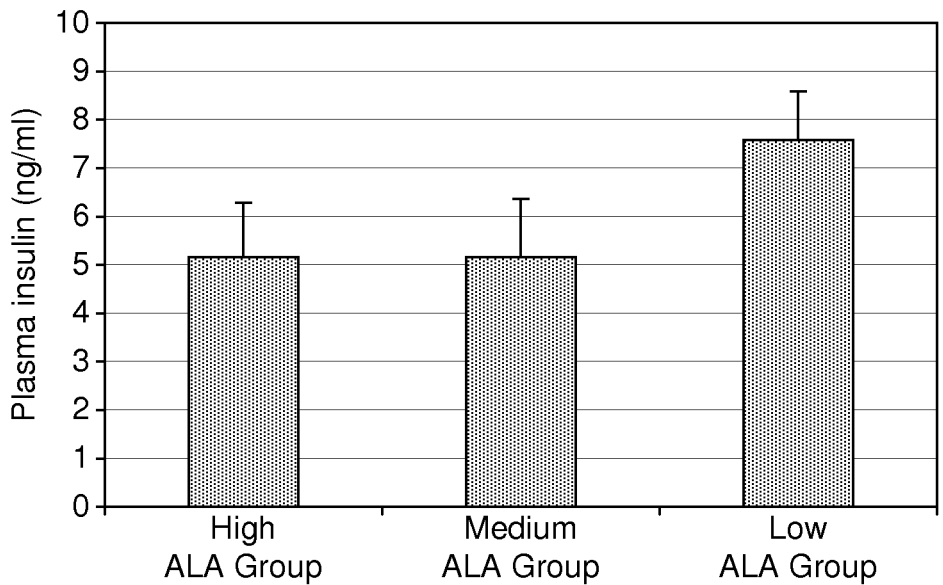
FIG. 6 shows the mean plasma insulin levels of the three groups at day 136.
Figure 7:
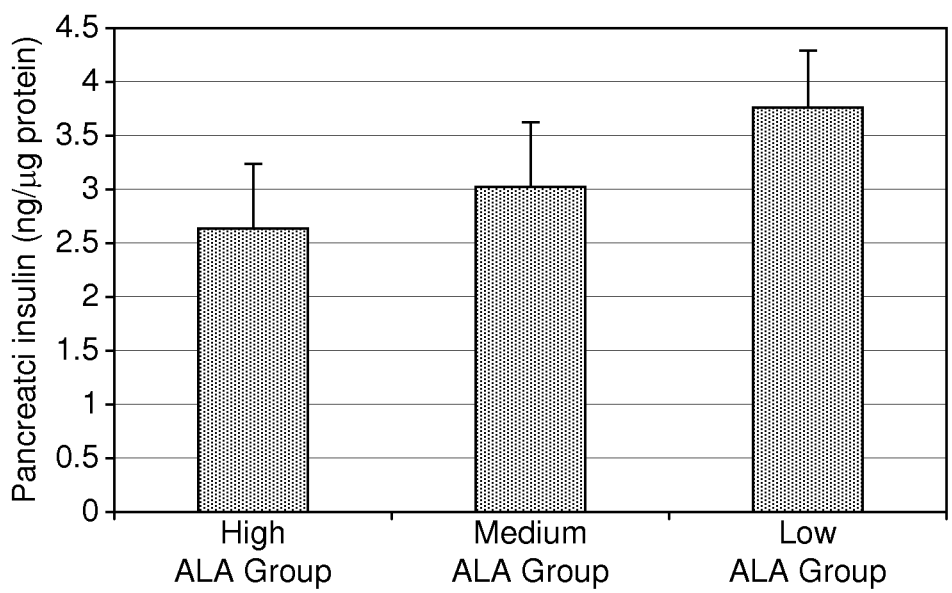
FIG. 7 shows the pancreatic insulin contents of the three groups at day 136.

Plasma insulin levels were not different between groups at day 21. However, as shown in FIG. 6, at the end of the experiment, the Low ALA group showed about a 1.5-fold higher concentrations of plasma insulin compared to the other two groups. FIG. 7 shows that similar results were observed regarding the pancreatic insulin content. The Low ALA group showed about a 1.4-fold increase in the pancreatic insulin content when compared to the High ALA group ($p=0.08$).

This example clearly demonstrates that feeding a diet rich in ALA during infancy plays an important role in programming or imprinting the adipose tissue in such a way as to reduce its susceptibility to excessive development later in life. Specifically, the results indicate that a low ALA intake with high LA:ALA ratio during the suckling/weaning period leads to increased adiposity and a tendency to hyperinsulinemia later in life.

Example 3

This example investigates the effect of feeding diets containing different amounts of LA and ALA to newborn guinea pig pups on the proliferation rates of adipose tissue cells (AT-cells) and on de novo lipogenesis (DNL) using the $D_2O$ method. The High ALA group and the Low ALA group from Example 2 were investigated. Ten pups in each group received $D_2O$ for 5 days prior sacrifice at day 21. The other 10 pups received $D_2O$ for 5 days prior sacrifice at day 136. The deuterated water was administered intraperitoneally (sterilized 0.9% NaCl, 99% $D_2O$ at 35 mg/g of body weight) in the morning of the first day. Thereafter, the pups drank deuterated water (8% enriched in deuterium) ad libitum for the remainder of the 5 days. They were then sacrificed by exsanguination under isoflurane anesthesia. The blood was collected from the aorta in heparinized vials (minimum of 200 μL). The retroperitoneal, epididymal and subcutaneous adipose tissues and the liver were collected and as well as the bone marrow from the rear-limb and kept at −80° C. until analysis.

The analytical procedure has been previously detailed (Neese R A, Siler S Q, Cesar D, Antelo F, Lee D, Misell L, Patel K, Tehrani S, Shah P, Hellerstein M K, "Advances in the stable isotope mass spectrometric measurement of DNA synthesis and cell proliferation" Analy Biochem 2001; 298: 189-195). Briefly, the genomic DNA of AT-cells and the triglycerides (TG) were extracted from the adipose tissues (about 50 mg). Deuterium enrichment in DNA and palmitate from TG were determined by mass-spectrometry hyphenated with gas-chromatography (GC/MS, Hewlett-Packard, Palo Alto, Calif.).

Use of $D_2O$ incorporation for the calculation of DNA replication (cell proliferation) and DNL is based on the precursor-product relationship (Hellerstein M K, Neese R. "Mass isotopomer data analysis: a technique for measuring biosynthesis and turnover of polymers" Am J Physiol 1992; 263: E988-E1001). In this method the cell divisions that occurred during the labeling period are counted by quantifying the proportion of labeled DNA strands present. The fractional proliferation rate of adipose tissue cells (FSRcell in % new cell/5 days) was calculated as the EM1 (isotopic enrichment in excess) in adipose DNA divided (normalized) by EM1 in bone marrow DNA. Bone marrow enrichment was used to approximate maximum DNA enrichment achievable within each animal.

DNL or "fractional synthesis rate of palmitate" (FSR-palmitate in % new palmitate/5 days) in TG was calculated from the label deuterium incorporation from water into TG-palmitate using mass isotopomer distribution analysis (MIDA). The present maximum deuterium enrichment reachable in palmitate was calculated based upon the measured body water enrichment (calculations are detailed in Hellerstein M K and Neese R A "Mass isotopomer distribution analysis at eight years: theoretical, analytic, and experimental considerations" Am J Physiol 1999; 276: E1146-E1170).

Results

The adipose tissue and liver weights are summarized in Table 6.

TABLE 6

Adipose tissue (AT) and liver weights (in g) at day 21 and day 136.

| Groups | Liver | Epididymal AT* | Retroperitoneal AT |
|---|---|---|---|
| | | d 21 | |
| High ALA | 8.57 ± 0.54 | 0.15 ± 0.02 | 0.56 ± 0.14 |
| Low ALA | 7.09 ± 0.40 | 0.09 ± 0.01 | 0.38 ± 0.06 |
| | | d 136 | |
| High ALA | 29.73 ± 2.15 | 8.09 ± 1.55 [a] | 9.36 ± 1.21 |
| Low ALA | 30.10 ± 1.11 | 10.94 ± 0.58 [b] | 10.98 ± 0.54 |

Different letters indicate statistical significance at P < 0.05.
*At d 136, P = 0.020 between High ALA/Low The effect of early diet treatment on the fractional synthesis rate (FSR or fractional proliferation rate) of cells in adipose depot is summarized in Table 7. The AT-cells include all type of cells such as the adipocytes and the stroma-vascular cells (pre-adipocytes, enterocytes, macrophages, etc.) of the whole adipose tissue.

TABLE 7

FSR (in % new cells/5 days) at d 21 and d 136

| Groups | Subcutaneous AT* | Epididymal AT | Retroperitoneal AT |
|---|---|---|---|
| | | d 21 | |
| High ALA | 8.9 ± 8.7 | 13.5 ± 2.0 | 5.3 ± 2.3 |
| Low ALA | 18.7 ± 13.7 | 15.0 ± 4.1 | 3.3 ± 0.7 |
| | | d 136 | |
| High ALA | 8.6 ± 1.7 [a] | 7.7 ± 1.3 | 4.0 ± 0.6 |
| Low ALA | 15.2 ± 1.3 [b] | 7.8 ± 2.6 | 7.9 ± 2.3 |

Different letters indicate statistical significance at P < 0.05.
*At d 136, P = 0.021 between High ALA/Low ALA These results show a higher (doubled) cell proliferation rate in the subcutaneous adipose tissue at day 136 (P=0.021) and a higher cell proliferation (but not significant) in the retroperitoneal and an unchanged cell proliferation in the epididymal adipose tissues in the Low ALA group compared with High ALA group. Since the subcutaneous adipose tissue is the major fat depot in the whole body of adult guinea-pigs, the increase of cell proliferation in this adipose tissue may explain the increased fat mass composition observed after a low ALA intake (results obtained in Example 2). Mechanistically, the results suggest that the increase in body fat mass in the Low ALA group involves an increase in the adipose tissue cell proliferation rate (a hyperplasia) in the guinea-pigs at the later adult period.

A low ALA intake did not induce changes in de novo lipogenesis (DNL) in the fat deposits but a higher hepatic DNL (P<0.001) was observed in the low ALA group as compared to the high ALA group at day 21 (Table 8).

TABLE 8

| | \multicolumn{4}{c|}{DNL (in % new palmitate/5 days) at day 21 and day 136} |
| Groups | Liver | Subcutaneous AT | Epididymal AT | Retroperitoneal AT |
|---|---|---|---|---|
| | | d 21 | | |
| High ALA | 8.8 ± 2.6$^a$ | 9.3 ± 6.6 | 14.9 ± 2.8 | 13.8 ± 5.4 |
| Low ALA | 17.4 ± 3.7$^b$ | 2.2 ± 1.8 | 17.1 ± 2.5 | 12.9 ± 2.3 |
| | | d 136 | | |
| High ALA | 5.7 ± 0.6 | 1.87 ± 0.26 | 1.18 ± 0.16 | 1.40 ± 0.39 |
| Low ALA | 5.6 ± 0.4 | 1.29 ± 0.18 | 0.92 ± 0.12 | 1.06 ± 0.07 |

Different letters indicate statistical significance at $P < 0.001$.

This example 3 shows that a low ALA intake during the suckling/weaning periods increases the rate of hepatic DNL in 21 days-old guinea pigs and increases the cell proliferation rate in the subcutaneous adipose tissue in adult guinea pigs.

The invention claimed is:

1. A nutritional composition comprising 4.4 to 6 g/100 kcal of the composition of a lipid source, 9 to 14 g/100 kcal of the composition of a carbohydrate source, and less than 1.85 g/100 kcal of the composition of a protein source wherein the lipid source comprises at least 16 wt % linoleic acid and 6 to 11 wt % α-linolenic acid expressed as a percentage of total fatty acid content in each case and the ratio of linoleic acid:α-linolenic acid is from 1 to 10, and the composition comprises arachidonic acid (ARA) and docosahexaenoic acid (DHA) in a ratio of 2:1 to 1:1 ARA:DHA.

2. A nutritional composition according to claim 1, wherein the linoleic acid content is from 18 to 30% of total fatty acids.

3. A nutritional composition according to claim 1, wherein the linoleic acid content is from 18 to 25% of total fatty acids.

4. A nutritional composition according to claim 1, wherein the α-linolenic acid content is from 2 to 12% of total fatty acids.

5. A nutritional composition according to claim 1, wherein the α-linolenic acid content is 10 wt % of total fatty acids.

6. A nutritional composition according to claim 1, wherein the linoleic acid:α-linolenic acid ratio is from 2 to 6.

* * * * *